US00RE38028E

(19) United States
(12) Reissued Patent
Briggs et al.

(10) Patent Number: US RE38,028 E
(45) Date of Reissued Patent: Mar. 11, 2003

(54) MOLECULAR GENETIC CONSTRUCTION OF VACCINE STRAINS OF PASTEURELLACEAE

(75) Inventors: Robert E. Briggs, Boone, IA (US); Fred M. Tatum, Ames, IA (US)

(73) Assignees: Biotechnology Research and Development Corporation, Peoria, IL (US); The United States of America as represented by the Department of Agriculture, Washington, DC (US)

(21) Appl. No.: 09/716,319

(22) Filed: Nov. 21, 2000

Related U.S. Patent Documents

Reissue of:
(64) Patent No.: 5,840,556
Issued: Nov. 24, 1998
Appl. No.: 08/770,234
Filed: Dec. 19, 1996

U.S. Applications:
(60) Provisional application No. 60/016,311, filed on May 8, 1996.

(51) Int. Cl.[7] ..... C12N 1/00; C12N 1/21; C12N 15/00; C12Q 1/68

(52) U.S. Cl. ..... 435/476; 435/67.1; 435/440; 435/471; 435/477; 435/243; 435/252.1; 435/252.3; 435/320.1; 536/23.1

(58) Field of Search ..... 435/6, 69.1, 440, 435/471, 476, 477, 243, 252.1, 252.3, 320.1; 536/23.1

(56) References Cited

U.S. PATENT DOCUMENTS 5,587,305 A 12/1996 Briggs et al.

FOREIGN PATENT DOCUMENTS

WO WO 97 16531 A1 5/1997

OTHER PUBLICATIONS

Briggs et al., "Isolation of a Cryptic Plasmic from *Pasteurella haemolytica* by Electroporation," Abstract, 72nd Annual Meeting of the Conference of Research Workers in Animal Disease, Nov. 11, 1991.

Craig et al., "A Plasmid Which Can Be Transferred Between *Eschirichia coli* and *Pasteurella haemolytica* by Electroporation and Conjugation" *J. Gen. Microbiology*, 135:2885–2890 (1989).

Homchampa et al., "Construction and Vaccine Potential of an Aro A Mutant of *Pasteurella haemolytica", Veterinary Microbiology* 42:35–44 (1994).

Briggs et al., "Characterizatin of a Restriction Endonuclease, PhaI, from *Pasteurella haemolytica* Serotype A1 and Protection of Heterologous DNA by a Cloned PhaI Methyltransferase Gene", *Applied and Environmental Microbiology* 60(6):2006–2010 (1994).

Tatum et al., "Molecular Gene Cloning and Nucleotide Sequencing and Construction of an aroA Mutant of *Pasteurella haemolytica* Serotype A1", *Applied and Environmental Microbiology* 60(6):2011–2016 (1994).

*Primary Examiner*—Sean McGarry
(74) *Attorney, Agent, or Firm*—Banner & Witcoff Ltd.

(57) ABSTRACT

Tools for genetically engineering Pasteurellaceae are provided. Replication-conditional plasmids which are useful for the Pasteurellaceae have been isolated and characterized. The plasmids can be utilized for delivery of DNA segments into the Pasteurellaceae in situations where control of extrachromosomal replication desired, such as in achieving allelic exchange or site-directed mutagenesis.

A restriction endonuclease, HsoI, was isolated from a bovine lung isolate of Haemophilus somnus. The enzyme was found to be a true isoschizomer of HinPI, a commercially available enzyme originally isolated from Haemophilus influenzae PI. Commercially available HhaI methyl transferase was found to protect against cleavage by both enzymes. Methylation of foreign plasmid DNA was found to enhance transformation of Haemophilus somnus in excess of four orders of magnitude.

17 Claims, No Drawings

MOLECULAR GENETIC CONSTRUCTION OF VACCINE STRAINS OF PASTEURELLACEAE

Matter enclosed in heavy brackets [ ] appears in the original patent but forms no part of this reissue specification; matter printed in italics indicates the additions made by reissue.

*Attention: More than one reissue application has been filed for the reissue of U.S. Pat. No. 5,840,556. The reissue applications are application Ser. Nos. 09/716,319 (the present application) and 09/971,575.*

This application claims benefit of priority under 35 U.S.C. 119(B) of Provisional application 60/016,311, filed May 8, 1996.

BACKGROUND OF THE INVENTION

Pasteurella haemolytica, P. multocida, and Haemophilus somnus are members of the Family Pasteurellaceae. Each is involved in respiratory disease syndromes in domestic cattle. These organisms have proven difficult to genetically manipulate, and therefore the construction of live, attenuated vaccines has been hampered.

Live attenuated bacterial strains generally provide superior protection as compared to killed bacterial vaccines (bacterins). In general, live vaccines elicit a stronger cell mediated response in the host than do bacterins. The superior immunity provided by attenuated live organisms may be explained by their ability to induce expression of stress-proteins and, possibly, of certain toxins within the host. The immune response generated by live organisms can be directed against these abundant proteins and thereby provide better protection.

There is a need in the art for live, attenuated vaccines against respiratory disease syndrome in domestic cattle caused by the Pasteurellaceae. There is also a need for techniques and tools to facilitate the construction of such vaccines.

SUMMARY OF THE INVENTION

It is an object of the invention to provide a replication-conditional plasmid.

It is another object of the invention to provide a cell-free preparation of a plasmid which is purified from genomic DNA and which is replication-conditional.

It is still another object of the invention to provide Pasteurellaceae host cells which comprise a plasmid which is replication-conditional.

It is an object of the invention to provide methods for introducing DNA into H. somnus.

It is an object of the invention to provide methods for mutagenizing H. somnus.

It is an object of the invention to provide H. somnus transformant strains.

It is an object of the invention to provide H. somnus mutant strains.

It is another object of the invention to provide genetically engineered H. somnus.

It is an object of the invention to provide a method of introducing a DNA segment into a Pasteurellaceae genome.

It is another object of the invention to provide genetically modified Pasteurellaceae.

These and other objects of the invention are provided by one or more embodiments described below. In one embodiment a plasmid which is conditional for replication in H. somnus, P. multocida, and P. haemolytica is provided.

In another embodiment of the invention a cell-free preparation of plasmid DNA is provided. The plasmid DNA is purified free of genomic DNA. The plasmid is temperature-conditional for replication in H. somnus, P. multocida, and P. haemolytica.

In another embodiment of the invention a host cell of the family Pasteurellaceae is provided. The host cell comprises a plasmid which is replication-conditional in H. somnus, P. multocida, and P. haemolytica.

In one embodiment of the invention, a method of introducing DNA to H. somnus is provided. The method comprises the steps of: providing a DNA molecule; methylating the DNA molecule with a methyl transferase enzyme having a recognition site of 5'-GCGC-3', to form methylated DNA; and transforming H. somnus cells with the methylated DNA.

In another embodiment of the invention a method for producing a mutation in a particular region of DNA of an H. somnus genome is provided. The method comprises the steps of: isolating a region of the genome from H. somnus; introducing a mutation into the region to form a mutated DNA region; methylating the mutated DNA region with a methylating enzyme which inhibits endonuclease cleavage at a recognition sequence 5'-GCGC-3' to form methylated DNA; introducing the methylated DNA into an H. somnus cell to form transformants; and screening the transformants for those which have the mutation in the region on chromosomal DNA of the H. somnus cell.

In yet another embodiment of the invention a preparation is provided of an isolated HsoI restriction endonuclease.

In still other embodiments H. somnus mutants and transformants made by the process of the invention are provided.

In another embodiment of the invention a method is provided of introducing a DNA segment to a Pasteurellaceae genome comprising: administering to a Pasteurellaceae cell a recombinant construct comprising the DNA segment and a plasmid which is temperature-conditional for replication in the Pasteurellaceae cell to form transformants; subjecting the transformants to a non-permissive temperature; screening the transformants for the presence of the DNA segment; and screening the transformants for the absence of the plasmid.

In yet another embodiment a genetically modified Pasteurellaceae is provided which is made by the method of administering to a Pasteurellaceae cell a recombinant construct comprising the DNA segment and a plasmid which is temperature-conditional for replication in the Pasteurellaceae cell to form transformants; subjecting the transformants to a non-permissive temperature; screening the transformants for the presence of the DNA segment; and screening the transformants for the absence of the plasmid.

These and other embodiments of the invention provide the art with the means to construct desirable mutants and transformants of the economically important and previously intractable Pasteurellaceae family of pathogens.

DETAILED DESCRIPTION OF THE PREFERRED EMBODIMENTS

In the generation of defined mutations in the Pasteurellaceae, it is desirable to introduce a segment of the genome carrying a defined mutation which has been made either in vitro or in another bacterium. Typically, the segment of the genome is introduced on a plasmid. In order to "transfer" the defined mutation from the incoming DNA to the genome, homologous recombination is required. A single recombination event will result in integration of the entire plasmid, which results in one wild-type and one mutant copy of the gene. A second recombination event is desirable, to delete the wild-type copy of the gene and the vector sequences. Since the occurrence of the desired double recombination is a rare event, occurring in only a fraction of the cells which receive the introduced DNA, increasing the number of cells which contain the introduced DNA will increase the recovery of cells which are double recombinants. The use of a plasmid which can replicate in the Pasteurellaceae increases the number of cells which have the introduced DNA. However, the presence of a plasmid in cells which may ultimately be used for vaccines is undesirable, as such plasmids often contain ecologically and medically undesirable drug- and toxin-resistance determinants.

The inventors have solved this problem by creating a plasmid which does not replicate under defined conditions, i.e., which is conditional for replication. Thus genomic DNA carrying a defined mutation introduced to cells via the plasmid can be present in many copies in many directly transformed and progeny cells, by growing the cells at the permissive temperature. This feature increases the absolute number of desired double recombinants obtained by increasing the starting population of cells carrying the DNA-segment. In addition, by switching to the non-permissive conditions (e.g., high temperature), one can eliminate plasmids which are episomal. It is a discovery of the present invention that placing such plasmid-bearing bacteria at a higher temperature which does not permit efficient plasmid replication, results in quick loss of the plasmid.

The conditionality of the replication of the plasmids of the present invention can be based on any selectable phenotype. For example, the plasmids might be unable to replicate in the presence of a particular agent, such as a drug or toxin. The plasmids might not be able to replicate in the presence or absence of certain metabolites or salts. Temperature-conditionality has been demonstrated for a mutant of pD70, but other conditionalities can be used, as well as other plasmids which replicate in the Pasteurellaceae. Particularly preferred are those plasmids of the same incompatibility group as pD70.

The plasmids of the present invention can be purified according to any art recognized method from genomic DNA Typical separations of plasmid from genomic DNA in a cell-free preparation are electrophoretic, chromatographic, density gradient sedimentation, alkaline lysis, etc. The plasmids can be introduced into bacterial host cells of the Pasteurellaceae by any means known in the art, including transformation, conjugation, liposome mediated gene transfer, particle bombardment, etc. Any Pasteurellaceae host can be used.

Plasmid mutations may be induced by any means known in the art. These include in vitro or in vivo chemical mutagenesis, passage through a mutator strain, etc. Even spontaneous mutations can be used if one is willing to screen more extensively. Particularly preferred are deletions and insertions which are non-reverting. Such mutations are easily generated in vitro using restriction enzymes, for example. Conditional mutations are most likely missense mutations, but nonsense mutations can also be used in the presence of a temperature-sensitive suppressor tRNA.

The temperature-conditional plasmids of the present invention can be administered to a Pasteurellaceae cell according to standard methods known in the art, including, but not limited to electroporation, transformation, transfection, transduction. One can screen by genetic or physical methods to detect those cells which have received the plasmid DNA Subsequently, one can screen among the plasmid recipients for those which have lost the plasmid and retained the DNA of interest carried on the plasmid. The screening methods can be genetic or physical, such as screening for a phenotype or screening for the presence of a particular DNA sequence in the cell by hybridization.

It is an additional discovery of the present invention that H. somnus contains a restriction-modification system, called herein the HsoI system. The HsoI restriction endonuclease has been isolated and its cleavage sequence determined to be 5'-GCGC-3'. It has also been discovered by the present inventors, that a barrier to transformation of H. somnus can be overcome by treating DNA with a methylating enzyme, such as the HsoI methyl transferase (M. HsoI). Such enzymes modify DNA substrates such that endonucleases which recognize 5'-GCGC-3' sequences are inhibited in their ability to digest such modified substrates. The methyl transferases produce a site which is 5'-GmCGC-3', i.e., the 5' cytosine is methylated. Examples of such methyl transferases are HsoI methyl transferase, HinPI methyl transferase, and HhaI methyl transferase, which is commercially available from New England Biolabs, Beverly, Mass., 01915. Cells containing such methyl transferase enzymes can also be used. Preferably, these are recombinant cells with the methyl transferase enzymes introduced, so that they lack the cognate restriction enzyme. Alternatively, they are mutant or natural variants which lack the cognate restriction enzyme. In some instances, it may be possible to passage DNA through cells which have both the restriction and methyl transferase enzymes, if the former is less active (slower) or less prevalent than the latter.

Methylation of DNA substrates for transformation (electroporation, or other means of introduction of DNA into cells) can be accomplished in vitro or in vivo. For in vitro methylation, DNA is incubated with a preparation of methyl transferase in the presence of a methyl donor, such as S-adenosylmethionine (SAM). In vivo methylation can be accomplished by passaging the DNA substrate through a bacterium which contains an appropriate methyl transferase, such as HsoI, HinPI, or HhaI methyl transferase. A mutant or natural variant of H. somnus which lacks the HsoI endonuclease could also be used to prepare DNA for subsequent introduction into H. somnus. Such a mutant can be made inter alia according to the method for site-directed mutagenesis disclosed herein.

Site-directed mutagenesis of H. somnus can be accomplished according to the present invention by first isolating a wild-type DNA region from H. somnus. A mutation is created in the isolated, wild-type DNA region according to any method known in the art. For example, the isolated DNA can be chemically mutagenized, either in a bacterium or in vitro. Alternatively, restriction endonucleases can be used to create precise deletions or insertions in vitro. Other methods as are known in the art can be used as is desirable for a particular application.

After H. somnus DNA has been isolated and mutagenized, it is methylated as described above. Then it can be introduced into H. somnus according to any technique known in the art, including but not limited to transfection, transformation, electroporation, and conjugation. Alternatively, rather than methylating the mutagenized DNA and introducing it into a H. somnus which expresses HsoI restriction endonuclease, one can omit the methylation of the mutagenized DNA and introduce the mutagenized DNA into an H. somnus, H. haemolyticus, or H. influenza cell which does not efficiently express the HsoI restriction endonuclease or an isoschizomer of it. Such cells can be isolated from nature by extensive screening, isolated following chemical mutagenesis of a cell which does express the HsoI restriction endonuclease, or made by the site-directed mutagenesis method disclosed herein. According to one aspect of the invention, the mutagenized and methylated H. somnus DNA region is introduced into a P. multocida cell on a plasmid which includes a P. haemolytica approximately 4.2 kb streptomycin resistance determining plasmid (pD70). This plasmid has also been deposited at the American Type Culture Collection, 12301 Parklawn Drive, Rockville, Md., 20852, USA, on Dec. 2, 1993, under the terms of the Budapest Treaty as Accession No. ATCC 69499. Derivatives of this plasmid or other pD70-incompatible plasmids can be used similarly. The origin of replication of pD70 can be isolated on a 1.2 kb Sau3AI fragment immediately downstream of the streptomycin resistance determinant. Gene conversion can be monitored inter alia by Southern hybridization with probes to the gene of interest, by screening for genetic markers on the introduced DNA construct (such as ampicillin® or streptomycin®), and by screening for the presence/absence of plasmid in the transformed cells' progeny.

Also provided by the present invention are mutant and transformant strains made by the disclosed methods of transformation and/or site-directed mutagenesis. Such mutants can provide the veterinary arts with attenuated, live strains of Pasteurellaceae, which are suitable for vaccines to induce protective immunity against Pasteurellaceae infection. For vaccine production, it is desirable that the mutation which attenuates the bacterium be an essentially non-reverting mutation. Typically these are deletion or insertion mutations, the latter not being caused by a transposable element. Strains which contain multiple attenuating mutations may also be used, so that the risk of reversion to a wild-type, virulent bacterium is vanishingly small.

Suitable attenuating mutants may be, for example, auxotrophic. Mutants with altered virulence factors may also be used.

One mutant strain which can be made by the site-directed mutagenesis method disclosed is one which is HsoI restriction endonuclease negative. Such a strain is useful for genetic engineering in H. somnus. Such a strain can be a recipient of DNA which is not HsoI methyl transferase methylated, yet would yield DNA which is HsoI methyl transferase methylated.

A preparation of isolated HsoI endonuclease can be prepared inter alia by passing a cell-free lysate of H. somnus over a column of heparin-sepharose. Other known techniques for isolating restriction endonucleases can be used as is appropriate. Typically the specific activity of such a preparation will be enriched as compared to the cell-free lysate.

The present invention thus allows those of ordinary skill in the art to stably introduce DNA into H. somnus. The DNA can be from other strains or species. The DNA can be artificially modified or in its native state. If recombination into the genome is desired two regions of flanking homology are preferred. Such techniques are generally known for other bacteria, but have been hitherto unsuccessful in H. somnus due to its restriction system.

Vaccines are typically formulated using a sterile buffered salt solution. Sucrose and/or gelatin may be used as stabilizers, as is known in the art. It is desirable that the Pasteurellaceae vaccines of the invention be administered by the intranasal or intratracheal route, but subcutaneous, intramuscular, intravenous injections also may be used. Suitable formulations and techniques are taught by Kucera U.S. Pat. No. 4,335,106, Gilmour U.S. Pat. No. 4,346,074, and Berget U.S. Pat. No. 4,957,739. Typically, between $10^7$ and $10^{11}$ CFU are administered per dose, although from $10^5$ to $10^3$ CFU can be used. Adjuvants also may be added.

EXAMPLES

Example 1

Plasmid Construction and Mutagenesis

The 4.2 kb plasmid (pD70) which encodes streptomycin resistance in Pasteurella haemolytica serotype 1 has been previously sequenced and described (Chang, Tatum). The plasmid was linearized by HindIII digestion and made blunt by treatment with dNTPs and Klenow fragment. A kanamycin cassette (Genblock) previously digested with BamHI and made blunt as above was ligated into pD70 to produce pD70kan. This plasmid was amplified in E. coli DH10B containing PhaI methyltransferase on cosmid PhaImtase. The plasmid was introduced into P. haemolytica strain NADC-D153. Plasmid DNA (1 ug) recovered from a kanamycin-resistant transformant was mutagenized with hydroxylamine for 90 minutes at 70° C. as previously described. The treated DNA was dialyzed against TE, ethanol-precipitated, and resuspended in TE (10 mM Tris, 1 mm EDTA, pH 8.0).

Example 2

Recovery of Temperature-Sensitive Plasmids.

Pasteurella haemolytica serotype 1, strain NADC D153, was grown to late logarithmic phase in 100 ml columbia broth at 37° C. with gentle shaking. The bacteria were pelleted by centrifugation at 5000 x G and washed in 100 ml 272 mm sucrose at 0° C. The pellet was resuspended in an equal volume of 272 mm sucrose at 0° C. Competent cells (100 ul) were placed into six 0.1 cm electroporation cuvettes and mixed with 100 ng of the treated DNA. The cells were electroporated (Gene pulser, Bio-Rad) at 18,000 V/cm and 800 ohms yielding time constants ranging from 11–12 msec. Immediately after each electroporation the cells were resuspended in 1.0 ml columbia broth at 0° C. Recovery was for 2 hours at 30° C. The suspension was spread (100 ul/plate) onto columbia agar (Difco) plates containing 50 ug/ml kanamycin. Plates were incubated 28 hours at 30° C. then transferred to 42° C. for 6 hours. Colonies were picked which were smaller than typical colonies and dotted onto kanamycin plates. After overnight incubation at 30° C., growth from each selected colony was duplicated onto columbia agar plates with and without kanamycin and then incubated overnight at 42° C. Growth from non-selective plates was transferred to kanamycin plates which were incubated overnight at 30° C. Clones which failed to grow with selection at 42° C. but which grew well on selective media at 30° C. after passage without selection at 42° C. were presumed to be temperature-sensitive for kanamycin expression. Similar clones which exhibited reduced growth on selective plates at 30° C. after passage without selection at 42° C. were presumed to be temperature-sensitive for plasmid maintenance. Four of the latter clones were selected for further study.

Example 3

Testing of Temperature-Sensitive Plasmids

Plasmid DNA was recovered by an alkaline lysis procedure from four P. haemolytica clones presumed to contain temperature-sensitive plasmid origins of replication. The DNA was electroporated into P. multocida strain NADC TT94, a bovine lung isolate which is Carter-Heddleston type A:3. After specific methylation with HhaI (as previously described) the DNA was electroporated into H. somnus strain HS91, a bovine lung isolate. Transformants were grown overnight on columbia agar plates supplemented with 5% bovine blood and 50 ug/ml kanamycin at 30° C. in 10% $CO_2$. Duplicate broth cultures were inoculated with transformants of each organism and plasmid. One culture was grown overnight at 40° C., the other at 30° C. Plasmid was recovered from each broth by an alkaline lysis procedure and resolved on 1% agarose gels. Selective and non-selective plates were struck for subjective assessment of percentage CFU resistant to kanamycin after passage.

Example 4

Properties of the Replication-Conditional Plasmid

Pasteurella haemolytica was transformed to kanamycin resistance by the mutagenized plasmid at an efficiency of about $6\times10^4$CFU/ug DNA. Of the transformants, about 1% (360) were found to form atypically small colonies after the incubation at 42° C. Passage of these colonies at either 30°C. or 42° C. on plates with or without kanamycin revealed that about 90% of the transformants were temperature sensitive for expression of kanamycin-resistance (about 10% failed to grow on the first passage and were not tested further). These organisms formed colonies on selective or non-selective plates at 30° C. but failed to grow on selective plates at 42° C. Passage of growth from non-selective plates at 42° C. to selective plates at 30° C. resulted in heavy growth, indicating plasmid was still present. A 5.5 kb plasmid was detected in plasmid preparations out of representatives of these cultures.

Ten of the 360 colonies behaved on passage similar to the colonies containing temperature-sensitive kanamycin genes except growth was reduced on selective media at 30° C. after passage without selection at 42° C. These colonies appeared to vary in percentage resistant to kanamycin after passage without selection at 42° C., indicating possible differences in their degree of instability at non-permissive temperature (42° C.). Four were selected based on their low yield of kanamycin-resistant colonies after passage without selection at the non-permissive temperature.

The four temperature-sensitive plasmids were readily introduced into P. multocida strain NADC-TT94 and into H. somnus strain NADC-HS91 (after appropriate methylation). The plasmids behaved as they did in P. haemolytica. No growth was observed on selective plates incubated at 40° C. and no plasmid was detected in broth cultures grown without selection at 40° C. Cultures transformed with wild-type plasmid grew well under selection at 40° C. and yielded plasmid DNA from non-selective broth cultures at that temperature. All cultures grew and yielded plasmid when grown with or without selection at 30° C. The results indicate that plasmid replication is temperature-conditional in each of the three species bacteria.

One of the temperature-conditional plasmids called pBB192 has been deposited in P. haemolytica NADC D153 at the American Type Culture Collection, Rockville, Md., 20852 under Accession No. ATCC 55893 on Dec. 2, 1996.

Example 5

Isolation and Characterization of Restriction Endonuclease, HsoI, from Haemophilus somnus and Protection of Heterologous DNA by HhaI Methyl Transferase.

Chromatographic fractions exhibiting endonuclease activity eluted from the heparin-sepharose columns by 680 and 760 mm NaCl (960–1060 $\mu$S). A single pass through these columns was sufficient to identify both the recognition specificity and cleavage site. Digestion of lambda DNA with the concentrated HsoI preparation resulted in a distinctive restriction fragment pattern identical to that produced by HhaI, a commercially available restriction endonuclease isolated from Haemophilus haemolytica. The cleavage site (5'. . . G↓CGC . . . 3') was found to differ from that of HhaI, producing a 5' overhang identical to that produced by HinPI.

Methods Used

Bacterium, growth, and crude extract.

Haemophilus somnus, strain 2336 (kindly supplied by Lynette Corbeil, San Diego, Calif.), was grown for 16 h on eight chocolate agar plates (Columbia blood agar base; Difco, Detroit, Mich., supplemented with 5% defibrinated bovine blood at 90 C, 200-ml total volume). The cells were harvested in TE (10 mm Tris, 1 mm EDTA, pH 8.0), pelleted by centrifugation at 16,000 x g for 5 min at 4 C, and washed once in TE. The washed pellet was resuspended in 12 ml chromatography running buffer (20 mm sodium phosphate, 10 mm 2-mercaptoethanol, pH 8.0, 0 C) and placed on ice. The bacterial cells were disrupted by sonication for 2 min in 15-s bursts. Debris and unbroken cells were removed by centrifugation at 16,000 x g for 10 min, and the supernatant was filtered through a 0.45-um-pore-size membrane (Millex-HA; Millipore Corp., Bedford, Mass.). No further treatment of the crude extract was performed prior to chromatography.

Chromatographic separation of proteins.

All chromatographic procedures were performed at room temperature. Prepacked heparin-Sepharose columns (Econo-pac heparin columns; Bio-Rad, Richmond, Calif.) were equilibrated as recommended by the manufacturer. A flow rate of 1.0 ml/min was used for separation, using a gradient low pressure automated chromatography system (Automated Econo-System; Bio-Rad, Richmond, Calif.). Five ml of crude extract was injected and a linear gradient from 0 to 1.0M NaCl in 60 ml of running buffer was used to elute proteins. Fractions (1 ml) were stored on ice prior to activity assay. A second identical chromatographic separation was performed with a new column from which active fractions were collected and pooled for storage.

Assay for restriction endonuclease activity.

Aliquots (5 ul) of the chromatographic fractions were incubated with 1 ul of React 1 (BRL, Gaithersburg, Md.) and 0.5 ul of unmethylated bacteriophage lambda DNA (0.5 ug/ul; New England Biolabs, Beverly, Mass.) at 37° C. for 2 h. After addition of tracking dye and electrophoresis on a 1% agarose gel in Tris-borate-EDTA buffer, the banding patterns were visualized by ethidium bromide staining and UV illumination. The fraction corresponding with DNA cleavage activity were pooled from the second chromatographic separation, concentrated 20-fold on 30,000-molecular-weight-cutoff ultrafilters, and brought to final concentrations of 150 mm NaCl, 10 mm sodium phosphate, 0.1 mm EDTA, 5 mm 2-mercaptoethanol, 0.25 ug of bovine, serum albumin per ml, and 50:50 (vol/vol) glycerol, pH 8.0, for storage at −20 C. The concentrated preparation was designated HsoI.

Determination of the recognition and cleavage sites for HsoI.

The recognition sequence was identified by digestion of pBluescript (Stratagene, La Jolla, Calif.) and of lambda DNA. The cleavage site was identified by digestion of a primed-synthesis reaction on pBluescript. An oligonucleotide primer was synthesized which is complementary with sequences 3' from an HsoI site of pBluescript. Singlestranded DNA was used for the template. Standard dideoxy DNA sequencing reactions were performed and an additional reaction containing no dideoxy terminator was extended through the HsoI site with the Klenow fragment of DNA polymerase I by using $^{32}$P-end-labeled primer. The extension reaction was stopped by phenol-chloroform extraction followed by ethanol precipitation. HsoI or HhaI (New England Biolabs) was added to the additional reactions and allowed to digest the DNA for 2 min. The reaction was stopped by addition of gel loading buffer and heating to 80° C. for 3 min.

Example 6

Transformation of H. somnus with Methylated DNA

DNA obtained from Haemophilus somnus or from E. coli and in vitro methylated with HhaI methyl transferase was resistant to cleavage by both HsoI and HhaI. Protection by in vitro methylation was found to often be partial, based on electrophoretic mobility of DNA after digestion with and without prior in vitro methylation, even when the substrate DNA had been phenol-chloroform-isoamyl alcohol extracted and then purified by CsCl gradient centrifugation.

Introduction of plasmid DNA into Haemophilus somnus was enhanced about 4 orders of magnitude by previous in vitro methylation of the plasmid. Each of the pD70-based plasmids transformed H. somnus, but efficiency dropped as the size increased. It is possible a second restriction-modification system may be responsible for the marked reduction in efficiency as plasmid size is increased. The possibility of systems analogous to mcr or mrr in E. coli was not investigated. Partial rather than complete protection conferred by in vitro methylation could also account for the reduction.

No ampicillin-resistant transformants were recovered, indicating either that the ampicillin-resistance cassette of pD80 does not express in H. somnus or that the origin of replication does not function. A pD70-based replicon containing the pD80 ampicillin-resistance cassette in the HindIII site transformed H. somnus to yield streptomycin-resistant colonies. Those colonies failed to replicate on ampicillin-containing media, indicating the ampicillin cassette does not function in H. somnus. The pD80 origin of replication was not tested further.

The kanamycin-resistance cassette derived from Tn903 was found to be excellent for selection of transformants. Streptomycin provided only fair selection. Transformants containing both streptomycin- and kanamycin-resistance cassettes were more robust on kanamycin selection than on streptomycin. Conversely, untransformed colonies were common on streptomycin selection but were not encountered on kanamycin selection.

A second strain of H. somnus, 649 (kindly supplied by Dr. Lynette Corbeil), was not transformed by derivatives of pD70. This strain was found to harbor a small plasmid which we presume to be incompatible with pD70. This plasmid, like pD70, might serve as a useful vector for the introduction of DNA into the bacterium.

The restriction-modification system carried by Haemophilus somnus are useful to genetically manipulate this pathogen. Specific methylation against the restriction endonuclease allows introduction of foreign DNA. Two replicons, both based on similar origins of replication, were discovered which may be of use as vectors for the introduction of foreign genes.

Methods Used

Construction and methylation of shuttle vector.

A derivative of pD70, the 4.2 kb streptomycin-resistance plasmid of Pasteurella haemolytica serotype 1, was previously constructed during experiments involving that bacterium. Briefly, the 2.2 kb PstI fragment of pD70 containing streptomycin-resistance was excised from a 1% agarose gel, electroeluted, and ligated with a PstI kanamycin cassette derived from Tn903.(Genblock, Pharmacia) The resulting plasmid conferred kanamycin-resistance in E. coli and in P. haemolytica. The plasmid was methylated with commercially available HhaI methyl transferase according to instructions. Other plasmids based on the pD70 origin of replication were tested, including intact pD70, pD70kan (pD70 with the kanamycin cassette blunt-ligated into the unique HindIII site), and pD80 (the 4.2 kb P. haemolytica plasmid encoding for ampicillin-resistance).

Electroporation of methylated DNA into Hemophilus somnus.

Haemophilus somnus strain NADC Hs91 (pneumonic bovine lung isolate) was grown in 100 ml Levinthol's broth at 37° C. in 10% $CO_2$ to late logarithmic phase, approximately four hours. The growth was pelleted by centrifugation at 5000 x G for fifteen minutes and washed once in 100 ml 272 mm sucrose at 0 C. The pellet was resuspended 1:3 packed bacteria: 272 mm sucrose on ice. Competent bacteria (100 ml) were mixed with 100 ng plasmid DNA either unmethylated or in vitro methylated in 0.1 cm electroporation cuvettes (Bio-Rad). The cells were quickly electroporated after addition of DNA (Gene pulser, Bio-Rad) at 18,000 V/cm, 800 ohm, 25 mFd with resultant time constants ranging from 11 to 15 msec. Levinthal's broth (1 ml, 0 C) was immediately added to the electroporated cells and the suspension was incubated at 25° C. approximately 10 minutes. The cells were then recovered at 37° C. with 10% $CO_2$ for 2 hours. Ten-fold dilutions were plated onto chocolate agar plates (Columbia blood agar base with 5% defibrinated bovine blood) containing 50 mg/ml kanamycin, 100 mg/ml streptomycin, or 20 mg/ml ampicillin. Colonies were enumerated after 36 hours incubation at 37° C. with 10% $CO_2$. Representative colonies were examined for plasmid content using a rapid alkaline lysis procedure.

Example 7

Use of a Temperature Conditional Replicon to Generate an aroA Deletion Mutant of Pasteurella multocida Previous attempts to produce gene-replacement mutants of P. multocida in our lab were hindered by poor electroporation efficiencies and by replication of ColE1-based replicons in P. multocida (unpublished results). In addition, products of gene-replacement typically contain foreign antibiotic resistance genes which may preclude or delay particular uses of otherwise desirable mutants. The shuttle plasmid constructed here was used to overcome those problems.

The origin of replication of the P. haemolytica plasmid pD70 was found to be within a 1.2 kb Sau3A1 fragment downstream from the streptomycin coding region. Together with a kanamycin cassette derived from Tn903, the vector (pBB192) proved to replicate in members of the Family Pasteurellaceae but not particularly well in E. coli, requiring cloning of sequences relying on the pD70 origin to be performed in a Pasteurellaceae host. While unsuitable for use in P. multocida, a derivative of the shuttle vector was constructed which contains a ColE1 origin of replication in the BamHI site (pBB192C) to facilitate construction in E. coli of temperature-conditional constructs for use in P. haemolytica or H. somnus target organisms (unpublished results). Plasmid pBB192C replicated efficiently in E. coli.

Approximately 100 P. multocida transformants were received on kanamycin at 30° C. from electroporation with 25 ng of replacement plasmid. Passage of broth cultures from 6 representative colonies to kanamycin plates at 40 C resulted in about 20 well isolated colonies from each 10 ul inoculum, but the number of colonies produced varied among the 6 cultures. The colony size varied significantly on each plate, yielding a number of small colonies and a few large colonies. The relative proportion of these sizes varied among the 6 cultures. Southern blot analysis of genomic DNA from the colonies (probing with aroA) revealed that the small colonies were products of single crossover events. The large colonies contained sequences homologous to aroA which were not similar in size to the replacement plasmid in addition to a fragment consistent with wild-type chromosomal aroA. The large colonies were not examined further. Our interpretation of the data is that the integrated replacement plasmid destabilizes the chromosome, resulting in a substantial reduction in replication rate and therefor conferring small colony size. The replacement plasmid, however, replicates so inefficiently by itself at the non-permissive temperature that colonies do not form at all under kanamycin selection. This situation put strong selective pressure to rearrange the plasmid for improved replication or to integrate into chromosome plasmid sequences containing the kanamycin gene, resulting in some potential unlikely products.

Passage of growth from products of single-crossover events without kanamycin selection resulted in >99% loss of kanamycin resistance in a single passage. These results indicate substantial instability of the single-crossover product. Among 500 isolated colonies from such a passage, 5 failed to grow on both defined medium and under kanamycin selection. Southern blot analysis confirmed the loss of DNA sequences homologous to the deleted ClaI-EcoRV fragment, failed to show homology with plasmid vector, and showed a reduction of about 300 bp in size of chromosomal aroA. Results of PCR analysis indicated a 300 bp reduction in product size. Sequencing of the PCR product confirmed a deletion extending from the EcoRV site to slightly beyond the ClaI site, 5'-ATTGATAT-GAACCAT-3', which does not alter the reading frame of downstream DNA sequences.

The temperature-sensitive shuttle vector separated the operations of bacterial transformation from that of selection of crossover products in gene-replacement. It also simplified the generation of products without foreign selectable markers. The instability of single-crossover products appeared to facilitate resolution of the plasmid from the chromosome to generate deletion mutants without use of negative selection afforded by such genes as SacB. Since the vector replicates temperature-conditionally in P. haemolytica and in H. somnus, it is likely that it should be equally useful in these or other Pasteurellaceae as well.

The P. multocida aroA mutant constructed here which was deposited on Dec. 2, 1996, at the ATCC, and given the accession number ATCC 55892, differs from that described by Homchampa et al because the present strain is of bovine origin, a deletion was introduced in aroA, and no foreign DNA sequences are present in the product. This mutant can be used as an attenuated live vaccine.

Methods Employed

Construction temperature-sensitive shuttle vector.

A shuttle-vector was constructed based on the previously described temperature-sensitive origin of replication of pD70, the streptomycin-resistance plasmid isolated originally from P. haemolytica serotype 1 (Tatum et al, Chang). A PCR product approximately 1450 bp was produced from temperature-sensitive pD70kan #192 using forward primer 5'-GCCTGTTTTTCCTGCTC-3' and reverse primer 5'-CCTGCGGTGTAAGTGTTATT-3'. The product was digested with Sau3A1 to completion to produce an approximately 1.2 kb fragment. A kanamycin resistance cassette from Tn903 (GenBlock, Pharmacia) was digested with EcoRI, ligated into the EcoRI site of pBC SK (Stratagene), and electroporated into E. coli strain 30-9G to produce PhaI-methylated plasmid DNA (Briggs et al). The approximately 1.3 kb kanamycin-resistance cassette was excised from the methylated plasmid with BamHI and ligated overnight to the 1.2 kb Sau3A1. The ligation mixture was electroporated into P. haemolytica strain NADC-D153 and plasmid was recovered from kanamycin-resistant colonies. It was found that a portion of the pBC SK multiple cloning site from the EcoR1 site to the BamHI site had been transferred along with the kanamycin cassette, resulting in a 2.5 kb plasmid with a unique EcoR1 site and an effectively unique BamHI site which replicates in P. haemolytica, P. multocida, and H. somnus at 30° C. but very poorly in E. coli. The plasmid was named pBB192.

Cloning and deletion of P. multocida aroA.

A 1.2 kb PCR product containing the aroA gene was produced using forward primer 5'-TTACTCTCAATCCCATCAGCTATA-3' and reverse primer 5'-CTATCTGTAGGCTACTTCGCGTG-3'. The product was cloned into a vector which contains EcoR1 sites flanking the PCR product insert (TA vector, Invitrogen). The insert was excised with EcoR1 and ligated into the EcoR1 site of puC9. The product was double digested with ClaI and EcoRV to remove an approximately 300 bp fragment. The ends of the remaining plasmid were made blunt using Klenow fragment of DNA polymerase I and dNTPs then ligated upon themselves to generate a deletion of aroA. The deleted plasmid was amplified in E. coli strain 30-9G to PhaI methylate the DNA then digested with EcoR1 and electrophoresed on an agarose gel to confirm the deletion. The PhaI-methylated EcoR1 aroA fragment containing the deletion was ligated into the EcoR1 site of pBB192 to create pBB192PmΔaroA. The ligation mixture was electroporated into P. haemolytica strain NADC-D153 and plasmid was recovered from kanamycin-resistant colonies.

Production of P. multocida single-crossover products.

Pasteurella multocida strain NADC-TT94, a bovine lung isolate of Carter-Heddleston type A:3, was grown 4 hours in 100 ml columbia broth containing 2,500 U hyaluronidase. Growth was centrifuged at 5000 x G for 15 minutes and washed twice in 272 mm and sucrose at 0° C. then resuspended in 1 ml 272 mm sucrose. The cells (100 μl) were electroporated (Gene Pulser, Bio-Rad) with 25 ng pBB192PmΔaroA in a 0.1 cm cuvette at 1.8 kv, 800 Ω, and 25 μF with a resultant time constant of 14.7 ms. The cells were immediately resuspended in 1 ml columbia broth at 0° C. then incubated for 2 hours at 30° C. The recovered cells were spread 100 ul/plate on columbia agar plates containing 50 μg/ml kanamycin then incubated 24 h at 30° C. Six colonies were passed separately to 5 ml columbia broth containing 50 μg/ml kanamycin which were incubated 18 hours at 30 C. Growth was spread (10 p/plate) onto columbia agar plates with kanamycin which were incubated 24 hours at 40 C. Representative colonies were passed to columbia broth (25 ml) with kanamycin (to confirm single crossover products by Southern blot analysis) and to columbia broth (5 ml) without kanamycin (to screen for deletion mutants) and incubated overnight at 40 C.

Screening for P. multocida deletion mutants.

From the non-selective broth culture above, columbia agar plates were struck for isolated colonies and incubated overnight. Five-hundred isolated colonies were passed into microtiter plates containing 100 μl columbia broth/well and incubated 6 hours. Growth (1 μl) was passed into each of two microtiter plates containing either 100 μl/well columbia broth with kanamycin or 100 μl/well chemically defined medium lacking tryptophane based on that of Wessman et al and that of Watko et al. Wells which grew only on the original non-selective microtiter plate but not on either kanamycin or defined medium were suspected deletion mutants. These were passed for Southern blot analysis and for PCR analysis using forward primer 5'-CTACCCACCTATCGCCATTC-3' and reverse primer 5'-TCCGCCCCCACCTTA-3'. The PCR product from one of the deletion mutants was cloned for sequencing of the deletion.

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: PASTEURELLA MULTOCIDA
(B) STRAIN: aroA- (xi) SEQUENCE DESCRIPTION: SEQ ID NO: 1:

ATTGATATGA ACCAT 15

(2) INFORMATION FOR SEQ ID NO: 2:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Pasteurella haemolytica
(B) STRAIN: serotype 1/pD70

(xi) SEQUENCE DESCRIPTION: SEQ ID NO: 2:

GCCTGTTTTT CCTGCTC 17

(2) INFORMATION FOR SEQ ID NO: 3:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO

-continued (vi) ORIGINAL SOURCE:
(A) ORGANISM: Pasteurella haemolytica
(B) STRAIN: serotype 1/pD70

(xi) SEQUENCE DESCRIPTION: SEQ ID NO: 3:

CCTGCGGTGT AAGTGTTATT 20

(2) INFORMATION FOR SEQ ID NO: 4:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Pasteurella multocida
(B) STRAIN: NADC-TT94

(xi) SEQUENCE DESCRIPTION: SEQ ID NO: 4:

TTACTCTCAA TCCCATCAGC TATA 24

(2) INFORMATION FOR SEQ ID NO: 5:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Pasteurella multocida
(B) STRAIN: NADC-TT94

(xi) SEQUENCE DESCRIPTION: SEQ ID NO: 5:

CTATCTGTAG GCTACTTCGC GTG 23

(2) INFORMATION FOR SEQ ID NO: 6:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Pasteurella multocida
(B) STRAIN: ATCC 55892

(xi) SEQUENCE DESCRIPTION: SEQ ID NO: 6:

CTACCCACCT ATCGCCATTC 20

-continued

```
(2) INFORMATION FOR SEQ ID NO: 7:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (A) ORGANISM: Pasteurella multocida
          (B) STRAIN: ATCC 55892

    (xi) SEQUENCE DESCRIPTION: SEQ ID NO: 7:

TCCGCCCCCA CCTTA                                                    15
```

We claim:

1. A method of introducing a DNA segment to a Pasteurellaceae genome comprising:

administering to a Pasteurellaceae cell selected from the group consisting of P. Multocida, P. Haemolytica, and H. somnus, a recombinant construct comprising the DNA segment and plasmid PBB192 which is temperature-conditional for replication in the Pasteurellaceae cell to form transformants;

subjecting the transformants to a non-permissive temperature;

screening the transformants for the presence of the DNA segment; and screening the transformants for the absence of the plasmid.

2. The method of claim 1 wherein the DNA segment is a transposable element.

3. The method of claim 1 wherein the DNA segment is a mutant form of the genomic DNA of the Pasteurellaceae.

4. The method of claim 3 wherein the mutant form is a deletion.

5. The method of claim 3 wherein the mutant form is an insertion.

*6. Isolated and purified bacterial cells of Pasteurella multocida aroA strain ATCC 55892.*

*7. Isolated and purified bacterial cells of Haemophilus somnus or Pasteurella multocida made by the process of claim 1.*

*8. Isolated and purified bacterial cells of Haemophilus somnus or Pasteurella multocida made by the process of claim 2.*

*9. Isolated and purified bacterial cells of Haemophilus somnus or Pasteurella multocida made by the process of claim 3.*

*10. Isolated and purified bacterial cells of Haemophilus somnus or Pasteurella multocida made by the process of claim 4.*

*11. Isolated and purified bacterial cells of Haemophilus somnus or Pasteurella multocida made by the process of claim 5.*

*12. The isolated and purified bacterial cells of claim 6 which is formulated with adjuvants.*

*13. The isolated and purified bacterial cells of claim 7 which is formulated with adjuvants.*

*14. The isolated and purified bacterial cells of claim 8 which is formulated with adjuvants.*

*15. The isolated and purified bacterial cells of claim 9 which is formulated with adjuvants.*

*16. The isolated and purified bacterial cells of claim 10 which is formulated with adjuvants.*

*17. The isolated and purified bacterial cells of claim 11 which is formulated with adjuvants.*

* * * * *

UNITED STATES PATENT AND TRADEMARK OFFICE

CERTIFICATE OF CORRECTION

PATENT NO. : RE 38,028 E
DATED : March 11, 2003
INVENTOR(S) : Robert E. Briggs et al.

It is certified that error appears in the above-identified patent and that said Letters Patent is hereby corrected as shown below:

Title page,
Item [56], References Cited, OTHER PUBLICATIONS, third reference, "Aro A" has been replaced with -- AroA --.

Signed and Sealed this

Thirteenth Day of April, 2004

JON W. DUDAS
*Acting Director of the United States Patent and Trademark Office*

UNITED STATES PATENT AND TRADEMARK OFFICE

CERTIFICATE OF CORRECTION

PATENT NO. : Re. 38,028 E
DATED : March 11, 2003
INVENTOR(S) : Robert E. Briggs et al.

It is certified that error appears in the above-identified patent and that said Letters Patent is hereby corrected as shown below:

Column 11,
Line 6, “received” has been replaced with -- recovered --;

Column 12,
Line 50, “and” has been removed.

Signed and Sealed this

Third Day of August, 2004

JON W. DUDAS
*Acting Director of the United States Patent and Trademark Office*